(12) United States Patent
Khosla et al.

(10) Patent No.: US 10,258,239 B2
(45) Date of Patent: Apr. 16, 2019

(54) METHOD FOR IN-LINE TESTING AND SURFACE ANALYSIS OF TEST MATERIAL WITH PARTICIPATION OF RAMAN SPECTROSCOPY

(71) Applicants: Vishal Khosla, San Jose, CA (US); Nick Doe, San Jose, CA (US); Ming Chan, San Jose, CA (US); Jun Xiao, San Jose, CA (US); Gautam Char, San Jose, CA (US)

(72) Inventors: Vishal Khosla, San Jose, CA (US); Nick Doe, San Jose, CA (US); Ming Chan, San Jose, CA (US); Jun Xiao, San Jose, CA (US); Gautam Char, San Jose, CA (US)

( * ) Notice: Subject to any disclaimer, the term of this patent is extended or adjusted under 35 U.S.C. 154(b) by 162 days.

(21) Appl. No.: 15/608,913

(22) Filed: May 30, 2017

(65) Prior Publication Data

US 2018/0344166 A1    Dec. 6, 2018

(51) Int. Cl.
  *A61B 5/00* (2006.01)
  *G01N 21/65* (2006.01)
  *G01N 3/56* (2006.01)

(52) U.S. Cl.
  CPC .......... *A61B 5/0075* (2013.01); *A61B 5/0071* (2013.01); *A61B 5/0082* (2013.01); *G01N 3/56* (2013.01); *G01N 21/65* (2013.01); *A61B 5/00* (2013.01); *G01N 2201/0826* (2013.01)

(58) Field of Classification Search
  None
  See application file for complete search history.

(56) References Cited

U.S. PATENT DOCUMENTS

| | | | |
|---|---|---|---|
| 4,516,060 A * | 5/1985 | Guzik | H02P 6/06 318/618 |
| 4,526,060 A | 7/1985 | Watanabe | |
| 5,760,950 A | 1/1998 | Maly et al. | |
| 7,839,496 B2 | 11/2010 | Borucki | |
| 7,944,555 B2 | 5/2011 | Claps | |
| 2008/0221457 A1* | 9/2008 | Zeng | A61B 5/0071 600/477 |
| 2008/0304074 A1* | 12/2008 | Brennan, III | A61B 5/0066 356/451 |
| 2012/0099102 A1 | 4/2012 | Bello | |
| 2013/0319071 A1* | 12/2013 | Vodnick | G01B 21/047 73/1.08 |

(Continued)

FOREIGN PATENT DOCUMENTS

| | | |
|---|---|---|
| CN | 102607977 | 1/2014 |
| WO | WO1966010737 | 4/1996 |

*Primary Examiner* — Clayton E. LaBalle
*Assistant Examiner* — Dennis Hancock (57) ABSTRACT

Proposed is a method for in-line testing and surface analysis of test material with participation of Raman spectroscopy wherein the apparatus has a column with a plurality of test units at least one of which is a wear test unit and another is a Raman spectrometer. The sample is located on a rotary table under the test units. By sequentially removing the material of the sample to a predetermined depth and then conducting the surface analysis with the use of the Raman spectrometer, it becomes possible to analyze distribution of the material components in the depth direction from the surface of the sample. delivery beams to the longitudinal axis of the Raman spectrometer

4 Claims, 5 Drawing Sheets

(56) References Cited

U.S. PATENT DOCUMENTS

| | | | |
|---|---|---|---|
| 2014/0002818 A1* | 1/2014 | Volodin | G01J 3/10 |
| | | | 356/301 |
| 2015/0075264 A1 | 3/2015 | Asif et al. | |
| 2016/0207825 A1 | 7/2016 | Black et al. | |
| 2017/0067735 A1* | 3/2017 | Khosla | G01N 19/00 |

* cited by examiner

METHOD FOR IN-LINE TESTING AND SURFACE ANALYSIS OF TEST MATERIAL WITH PARTICIPATION OF RAMAN SPECTROSCOPY

FIELD OF THE INVENTION

The present invention relates to the field of tribology, in particular for in-line testing mechanical properties and surface analysis of the material including determination and distribution of components in the matrix of a test material by utilizing Raman spectroscopy. More specifically, the invention relates to a method for in-line testing and surface analysis of a test material where the test can be conducted with multiple sequential measurements of the material physical properties such as harness, resistance to wear, friction properties, etc., along with determination of material composition components and their distribution in the depth direction from the specimen surface revealed by using Raman spectroscopy.

BACKGROUND OF THE INVENTION

During a tribology test, the engaging surfaces of two samples are brought in contact to measure friction and wear. In a reciprocating, rotary, fretting, or oscillating test, one of the samples may move while the other sample remains stationary. In some cases, the upper sample may be stationary while in other cases the upper sample may be moveable. The test requires applying a known force and studying the effects of force, speed, time, temperature, or other factors of friction, wear, life of coatings or bulk materials, lubricants, fluids, etc. In tribology, important parameters are load, stroke, speed, and environmental conditions.

A variety of methods and apparatuses can be used for measuring and analyzing the results of tribology tests. Such methods and apparatuses can be classified as mechanical, electrical, and optical. Each of these groups offers a different implementation. For example, a scratch test measures the adhesion or hardness of coatings or matrix materials. Typically, such a test involves moving a sharp tip for a fixed distance at a known velocity under an increasing or constant load. The final scratch marks are analyzed (during and after test) to calculate adhesion or hardness of the material. Such methods and apparatus are available in a variety of modifications, one of which is a tester coupled with an atomic force microscope.

For example, US Patent Application Publication 2015/0075264 issued in 2015 discloses an optical microscope used for pre-inspection of a subject, wherein an atomic force microscope (AFM) integrated with the optical microscope is passed over a subject and the subject surface is scanned according to the measured deflection of the AFM cantilever. A laser is directed at the cantilever, and the reflected laser light is incident on a photodiode that accordingly detects deflection of the cantilever. The AFM cantilever deflects according to one of the mechanical contact forces, van der Waals force, capillary forced, chemical bonding, electrostatic force, magnetic force, etc.

One of the advanced methods in the field of material testing is the use of confocal microscopy (see. e.g., U.S. Pat. No. 7,839,496 issued on Nov. 23, 2010 to Leonard J. Borucki). The invention relates to a sample holder for confocal microscopy of chemical mechanical polishing (CMP) pad samples cut or otherwise removed from either new or used CMP pads that maintains uniform load and pressure over the part of the sample visible to the confocal microscope.

U.S. Pat. No. 5,760,950 issued on Jun. 2, 1998 to Maly, et al, discloses a scanning confocal microscope optical system for forming an image of a subject illuminated by light from an illumination system that includes a Nipkow disk arranged perpendicular to a light propagation path and that has a surface on which a plurality of pinholes are distributed substantially symmetrically about an axis perpendicular to the surface of the disk. The system further includes components for projecting an image of a first set of pinholes onto a second set of pinholes, the image being formed of light transmitted by the first set of pinholes when the first set is illuminated by light that impinges on the first side of the disk. The system further includes a collective lens and a first objective lens for focusing light transmitted by the second set of pinholes onto the subject and for collecting light reflected by the subject. The first objective lens has a large numerical aperture. Light reflected by the subject passes through the second set of pinholes. Finally, the system may include a device for spinning the Nipkow disk about the axis.

Chinese Patent No. 102607977 B issued in 2014 describes an abrasion in-situ measuring device and a method based on digital image processing. This device comprises an attachment to a universal material tester and contains a frame attachable to the base of the tester and supporting sliders moveable in the directions of X, Y, and Z axes, one slider of which carries a digital microscope that can be used for recording the results of testing in situ and for subsequent analysis of the recorded data.

Known in the art are also tribology testers which combine determination of physical properties of the materials, e.g., by scratch testing, by using Raman spectroscopy for determination of components of the test material, etc. Although it is not strictly correct, for convenience of the description let us call such determination of test material components as determination of "chemical properties" of the test material.

For example, US Patent Application Publication No. 20160207825 A1 published on Jul. 21, 2016 (Inventors: M. Black, et al.) discloses testing of strength of a laminated material by using Raman microscope. The Raman measurements are obtained at two different wavelengths, 442 nm and 514 nm. The dominant peak observed is the "G" peak that is related to $sp^2$ bond stretching graphitic modes in the polymeric scratch resistant layer. The Raman measurements are taken at two different wavelengths to assess the shift in the "G" peak position with excitation energy, allowing the measurement of the dispersion. The dispersion is useful in determining the atomic bonding in the polymer scratch resistant layer.

The samples are also measured to determine the thickness of a polymer scratch resistant layer using ellipsometry. The samples are also tested with a nano-indentation test using a Berkovitch diamond indenter. The Berkovitch diamond indenter is used to furrow scratches into the surface of the polymeric scratch resistant layer of each sample. In the test, the tip of the Berkovitch diamond indenter is brought into contact with the surface of the sample. One or more aspects of the disclosure pertained to a laminate including a substrate, such as a glass substrate, which may be strengthened, or a sapphire substrate, and a polymer scratch resistant layer disposed on the substrate. In one or more embodiments, where a glass substrate is utilized, the average flexural strength of the glass substrate is maintained when combined with the polymeric scratch resistant layer.

International Patent Application Publication No. WO 1996010737 A1 (issued on Apr. 11, 1996; Inventors: G. Pitt, et al.) discloses a scratch tester, in which a film or coating on a sample is scratched by a stylus in order to examine qualities such as its cohesion or adhesion to the substrate. Simultaneously or subsequently, the scratched surface is illuminated by laser light, e.g. through a microscope, in order to generate Raman scattered light. The Raman scattered light passes back through the microscope and is analyzed to determine stresses or strains present in the scratched region. This enables the determination of quantitative information about the quality of the film or coating. Similar Raman analysis methods may be used in indentation testing and tribological testing.

However, the delivered laser light and the received Raman irradiation are supplied and received through a common channel, and this involves subsequent problems in connection with separation of a useful signal from the luminescence background signal.

U.S. Pat. No. 7,944,555 B2 issued on May 17, 2011 to R. Claps relates to medical application of high-speed, rugged, time-resolved, Raman spectroscopy for sensing multiple components of a sample and for diagnostics of pathological skin conditions such as cancer. One embodiment of the device employs a rotating optical switch to time multiplex an input signal through multiple band-pass filters and into a single optical detector which is electrically activated only when the filtered input light pulse is about to impact it. Time-multiplexing the input signal through multiple optical filters and time-sequencing the optical detector enables to accelerate the analysis. One embodiment shows a system for Raman spectroscopy which employs multiple lasers, which provide signals of different wavelengths $\lambda_1$, $\lambda_2$, $\lambda_3$, respectively. These signals are transmitted to a time-division multiplexer which has thereon an optical system which allows these signals to be transmitted in sequence to a sample. The Stokes radiation scattered from the samples sent to optical circulator and from there is sent to a notched filter that blocks the signals with wavelengths $\lambda_1$, $\lambda_2$, and $\lambda_3$ but which passes the stokes radiation associated with these wavelengths. Optical filter, although a blocking filter for the wavelengths $\lambda_1$, $\lambda_2$, and $\lambda_3$, is a single band-pass or band-block filter for the Stokes radiation. This combined filter is made possible by the large spectral range between the illumination radiation and the Stokes radiation in most Raman signals.

US Patent Application Publication No. 20120099102 A1 published on Apr. 26, 2012 (Inventor: J. Bello) discloses a dual and multi-wavelength sampling probe for Raman spectroscopy. The application relates to optical probes and methods for conducting Raman spectroscopy of a material at multiple excitation wavelengths. The probes and methods utilize optical elements to focus outputs from a plurality of light sources or lasers onto a sample, collect backscattered light from the sample, separate Raman spectra from the backscattered light, and provide at least one output containing the spectra. By utilizing multiple excitation wavelengths, the probes and methods avoid Raman measurement issues that may occur due to, for example, fluorescence and/or luminescence. A disadvantage of the proposed Raman sampling probe is that the excitation laser light and the received Raman radiation are delivered and received through a common channel which inevitably creates problems in subsequent separation of the signals.

However, all apparatuses for in-line testing and surface analysis of test materials with participation of Raman spectroscopy have a linear arrangement of test and measurement stations and therefore such apparatuses occupy a large floor space. Another disadvantage of linear in-line-test and surface-analysis apparatuses is that they cannot ensure high accuracy in reinstallation of the test and measurement units in the same point of interest over the test sample. On the other hand, the use of a Raman spectroscopy probe for analyzing distribution of the material components in the depth direction during wear test requires high accuracy for observing conditions of wear or destruction in the same point of interest.

SUMMARY OF THE INVENTION

A distinguishing feature of the material test method of the invention for in-line testing and surface analysis of a test material with participation of Raman spectroscopy consists of a unique arrangement of test and measurement units of the test apparatuses which are installed on a column above a rotary platform that rotates relative to the test and measurement units and carries a test specimen. The above feature is especially important for analyzing distribution e.g., of an alloy component in an alloy matrix, from the surface in the depth direction of the specimen or from the surface in the depth direction of the coating, or the like, especially in a test with a layer by layer removal of the material, e.g., in a wear test. In such applications, a Raman spectrometer becomes an indispensable part of a material tester since the unique features of the Raman tester of the present invention makes it possible to conduct Raman analysis repeatedly many times in the same point of interest, e.g., after wear of the surface layer for a given number of wear cycles.

Furthermore, an advantage of the material tester with rotary arrangement of the test and measurement units over the test with the linear motion of the respective units is that application of any forces to the specimen in a tangential direction does not exert any harmful action on the accuracy of multiple positioning in the same point for repeated measurements.

DETAILED DESCRIPTION OF THE INVENTION

A distinguishing feature of the material test apparatus of the invention (hereinafter referred to in some places as a tester) for in-line testing and surface analysis of a test material with participation of Raman spectroscopy consists of a unique arrangement of test and measurement units of the tester which are installed on a vertical column of the tester and a rotary table that carries a sample holder with a sample that can be repeatedly installed with high accuracy in the same position under the test and measurement units. The above feature is especially important for analyzing distribution e.g., of an alloy component in an alloy matrix, from the surface in the depth direction of the specimen or from the surface in the depth direction of the coating, or the like, especially in a test with a layer by layer removal of the material, e.g., in a wear test. In such applications, a Raman spectrometer becomes indispensable part of a material tester since the unique features of the Raman tester of the present invention makes it possible to conduct Raman analysis repeatedly many times in the same point of interest, e.g., after the wear of the surface layer with a given number of wear cycles.

Figure 1:
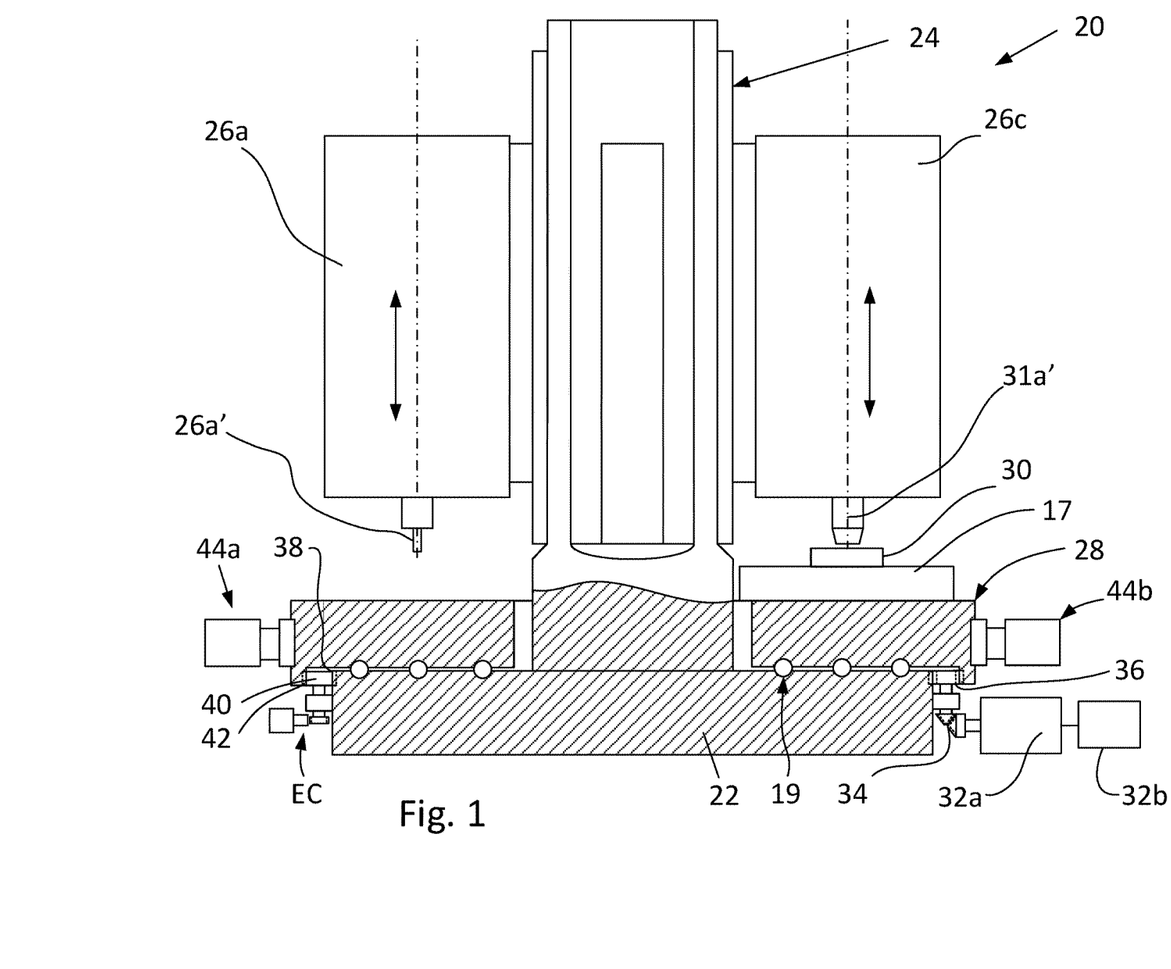
FIG. 1 is a vertical partially sectional view of the apparatus of the invention for in-line testing and surface analysis of test materials with participation of a Raman spectrometer of the invention.
Figure 2:
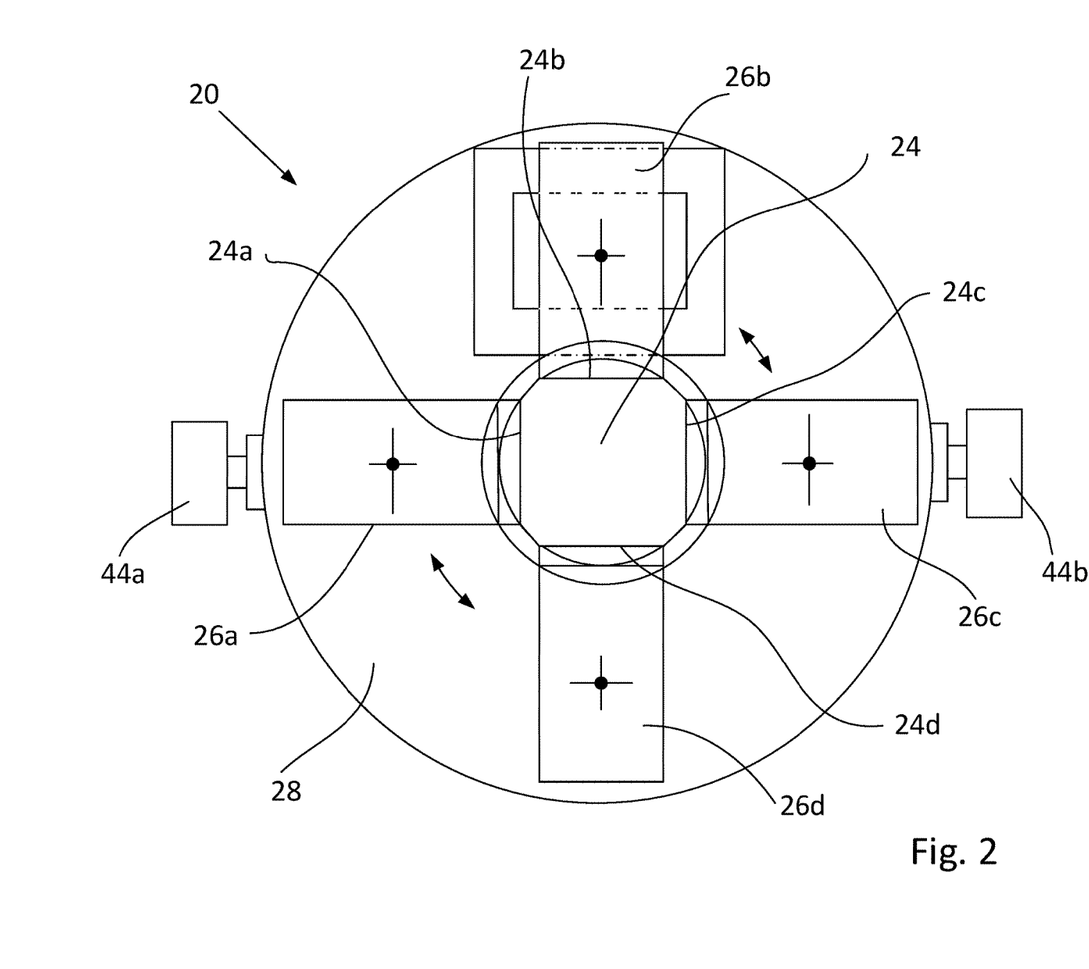
FIG. 2 is a top view of the tester of FIG. 1.

FIG. 1 is a vertical partially sectional view of the apparatus of the invention for an in-line testing and surface analysis of a test material with participation of a Raman spectrometer of the invention, and FIG. 2 is a top view of the tester of FIG. 1.

As can be seen from the above drawings, the tester 20 has a stationary base plate 22 that preferably has a round shape and supports a vertical column 24, which has vertical flats (four in the illustrated example), i.e., 24a, 24b, 24c, and 24d.

A plurality of test units such as a wear test unit 26a, a hardness test unit 26b, a Raman spectrometer 26c, and a scratch test unit 26d are installed in predetermined positions on the vertical column 24. The test units are installed on respective flats of the column and can move in a vertical direction as shown by arrows in FIG. 1. Reference numeral 26a' designates a wear test probe.

The base plate 22 rotationally supports a rotary table 28, which rests on a thrust bearing 19 formed by a number of concentric grooves with balls. The rotary specimen table 28 supports at least one specimen 30 placed on a specimen holder 17. The rotary specimen table 28 is driven into rotation from a motor 32a with a driver 32b via a bevel gear pair 34 and parasitic gears 36 which rolls around a stationary gear rim 38 formed on the base plate 22 and transmits rotation to an internal gear wheel 40 formed on the inner surface of the gear rim 42 of the rotary specimen table 28.

Reference numerals 44a and 44b designate stoppers that stop the rotary table 28 in a selected position of the sample 30 on the sample holder 17. In other words, the stoppers lock the rotary table 28 during application of measurement forces to the specimen 30, e.g., during the wear test.

Symbol EC designates an encoder mechanism of the type disclosed in U.S. Pat. No. 4,516,060 issued to N. Guzik, et al. on May 7, 1985. The purpose of the encoder EC is to provide a precision circular measurement position of the respective test unit over the sample in the course of repeated tests.

Figure 7:
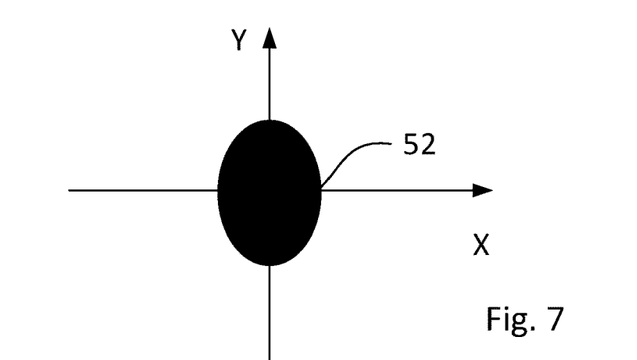
FIG. 7 is a view of a light spot formed on the laser light illumination plane.

Linear movements of the sample holder 17 with the sample 30 in the X-Y plane (FIG. 7) is carried out by means of the same mechanism as one shown in FIGS. 2a and 2b of pending U.S. patent application Ser. No. 14/848,749 filed on Sep. 9, 2015 by the same applicants (V. Khosla, et al.).

The advantage of the rotary motion over the linear is that application of any forces to the sample in a tangential direction does not exert any harmful action on the accuracy of repeated positioning of the sample in the same point relative to the measurement station for repeated tests and measurements.

In investigation of carbon materials, the apparatus of the invention equipped with the specific Raman spectrometer of the invention (hereinafter referred to as "apparatus of the invention") allows determination of carbonaceous hybridization (for a diamond the peak is at 1332 $cm^{-1}$, for graphite—in the range of 1550-1580 $cm^{-1}$). It also allows to observe inclusion of impurity phases, distribution of phases in composites, evaluate thickness of carbon coatings, study processes of intercalation in graphite, and study processes of pyrolysis at elevated temperatures (if the device is provided with a high-temperature accessory unit). The apparatus of the invention also allows low-temperature measurements (down to the temperature of liquid helium). It should be noted that investigation of unstable samples requires use of low-power lasers.

In investigation of inorganic materials, the apparatus of the invention allows analysis of polymorphic modifications, determination of distribution of phases with high spatial resolution, determination of impurities adsorbed on surfaces, investigation of processes of metal corrosion (in combination with the use of a Raster Electron Microscope), as well as investigation of luminescent samples (with mapping and at a low temperature). In studying thin coating, the laser wavelength should be selected so as to maximize absorption of the phase being investigated and to minimize luminescence of other phases.

In investigation of epitaxial films, the apparatus of the invention makes it possible to determine dispersion curves for backgrounds and background densities. It allows to reveal and map micro-stress.

Normally, investigation of thin solid multicomponent coatings with conventional Raman spectroscopy encounters a problem associated with the fact that absorption of a target phase is "contaminated" with luminescence from concomitant phases. Therefore, it is difficult to obtain a clear and accurate result. This problem is solved by the specific structure of the Raman spectroscopy probe offered by the present invention. Furthermore, according to one modification of the apparatus of the invention it is possible to perform mapping of surface luminescence, reveal micro-stress in thin epitaxial solid coatings, and find a specific wavelength most optimal for carrying out the above processes.

According to another modification of the apparatus of the invention it becomes possible to accelerate mapping of surfaces by focusing the laser beam into linear sections.

Figure 3:
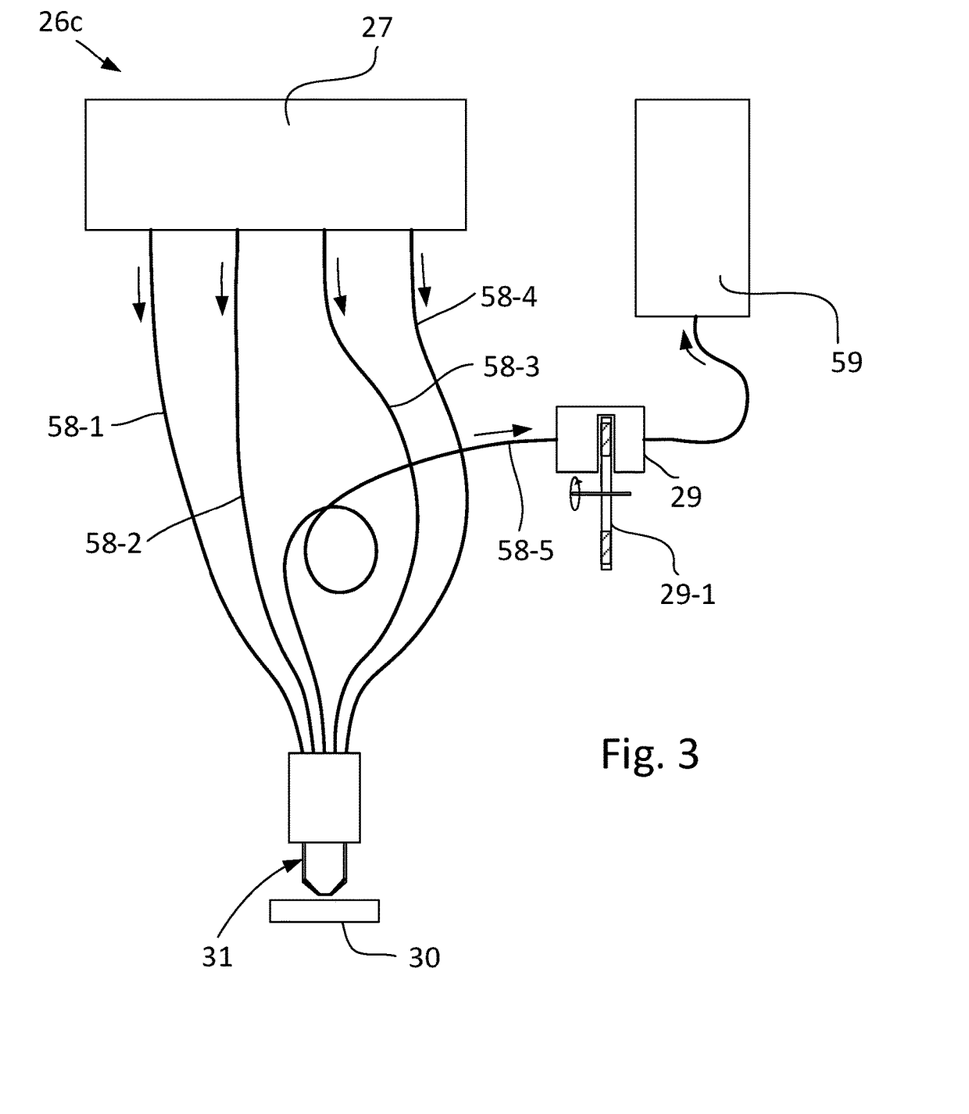
FIG. 3 is a block diagram of the Raman spectrometer unit of the invention used in the tester of the invention.

FIG. 3 is block diagram of the Raman spectrometer 26c of the invention used in the tester of the invention (FIG. 2). In FIG. 3, reference numeral 27 designates a laser unit that contains a plurality, e.g., four lasers (not shown) which are coupled with respective four optical fiber optical fiber waveguides 58-1, 58-2, 58-3, and 58-4. The arrows in FIG. 3 show direction of light propagation. Reference numeral 29 designates a filter block which contains a set of optical filters, one of which, is shown in FIG. 3 and is designated by reference numeral 29-1. Such filters are intended to block the passage of the signals of luminescence and the reflection through a waveguide 58-5 to a spectrum analyzer unit 59.

In general, such an arrangement of optical fiber waveguides, filters and other components of a spectrometer assembly are known in art and beyond the scope of the present invention (see USH 2002H1).

Reference numeral 31 designates a multi-wavelength Raman spectroscopy probe, which will be described below in more detail with reference to FIG. 4. As can be seen from FIG. 1, during the test with the use of the Raman spectrometer 26c the multi-wavelength Raman spectroscopy probe 31 is arranged above the sample 30 being tested. The Raman signal collected by the multi-wavelength Raman spectroscopy probe 31 is guided via the Raman radiation receiving waveguide 58-5 to the spectrum analyzer unit 59 (FIG. 3).

Figure 4:
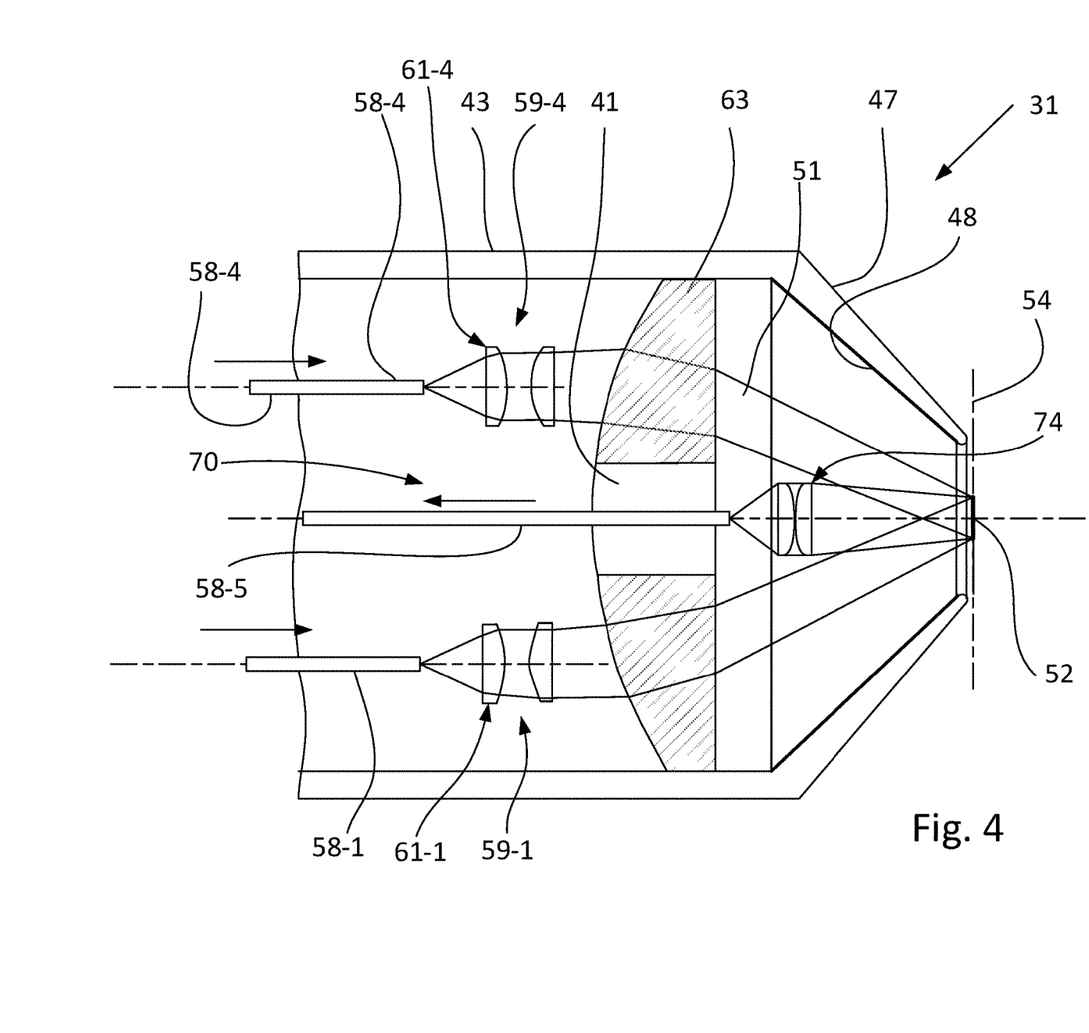
FIG. 4 is schematic view of a Raman spectroscopy probe used in the Raman spectrometer unit of the invention.

The structure of the multi-wavelength Raman spectroscopy probe 31 is shown in more detail in FIG. 4. The multi-wavelength Raman spectroscopy probe 31 has four light transmitting channels, only two of which, i.e., 59-1 and 59-4 are shown in FIG. 4. Each channel includes the respective optical fiber waveguide (58-1 and 58-4, respectively), a micro-collimator (two of which, i.e., 61-1 and 61-4, are shown in FIG. 4), and a part of a common light-beam tilting lens 63, which has a property of tilting the laser beams that pass therethrough in a converging manner towards the point of interest at a predetermined angle relative to said longitudinal axis of the Raman spectrometer 31.

Reference numeral 70 designates a data collection channel that consists of a Raman radiation receiving waveguide 58-5 and a light collecting lens assembly 74 which collects radiation from a light spot 52 formed by excitation beams on the plane 54 that coincides with the test surface of the sample 30. The housing 43 of the multi-wavelength Raman spectroscopy probe 31 has a tapered front end 47 the inner surface 48 of which is blackened for absorbing the parasitic scattered light and hotspots. The common light-beam tilting lens 63 has a central opening 41 for passing the waveguide of the Raman radiation receiving waveguide 58-5 that delivers the collected Raman signals to the spectrum analyzer unit 59 (FIG. 3).

Figure 5:
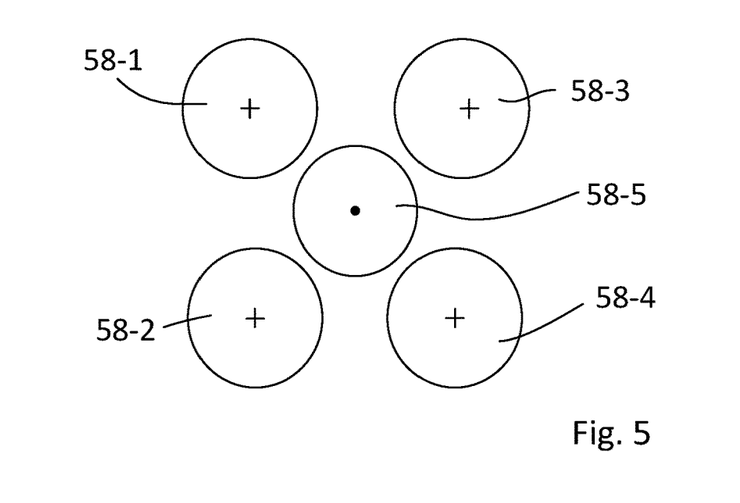
FIG. 5 is a simplified transverse sectional view of the Raman spectroscopy probe illustrating arrangement of laser light transmitting channels and a Raman radiation receiving channel.

FIG. 5 is a simplified transverse sectional view of the Raman spectroscopy probe 31 illustrating arrangement of laser illumination channels 58-1, 58-2, 58-3, 58-4 and a Raman radiation receiving channel having a Raman radiation receiving waveguide 58-5.

Figure 6:
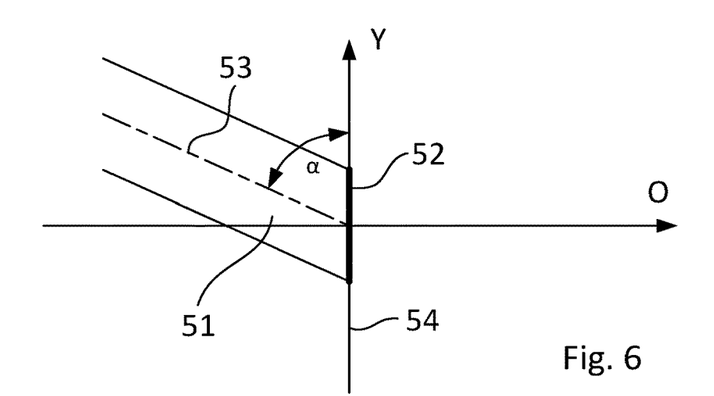
FIG. 6 is a view illustrating one of laser light delivery beams tilted at a certain tilt angle α to the illumination plane Y-X.

As shown in FIG. 4, when the laser light beam such as a beam 51 propagates through the channel 59-4 (although four such channels exists, only one will be considered for simplification of the description), the common light-beam tilting lens 63 tilts the laser light delivery beam 51 inward of the multi-wavelength Raman spectroscopy probe 31 at a certain angle α of the central axis 53 of the beam to the longitudinal axis O-O of the Raman spectrometer (see FIG. 6, which is a view illustrating one of laser light delivery beams, e.g., the beam 51). When the beam 51 falls onto the plane 54, it forms a light spot 52 having a substantially elliptical shape shown in FIG. 7.

The tilt angle α, at which the laser light delivery beam 51 is inclined to the longitudinal axis O-O of the Raman spectrometer, is selected so as to minimize access of the undesirable excitation light reflected from the illuminated surface to the Raman radiation receiving waveguide 58-5, and hence, to the spectrum analyzer unit 59 (FIG. 3).

In view of a variety of possible test materials and necessity of selecting the angle α most optimal for obtaining reliable data and the best noise/signal ratio, the apparatus of the invention is provided with a set of multi-wavelength Raman spectroscopy probe heads 31. This set has to cover a relatively wide range of angles α, e.g., in the range of 30° to 75°, preferably 40° to 60°.

In operation of the apparatus of the invention, first one multi-wavelength Raman spectroscopy probe 31 is selected from the set of such probes with different angles of tilt of the laser light delivery beams 51 to the longitudinal tester of the Raman spectrometer. The rotary table 28 is turned into a position in which the point of interests on the sample 30 is aligned with the position of the multi-wavelength Raman spectroscopy probe 31. Stopping of the table 28 in a precise position under the multi-wavelength Raman spectroscopy probe 31 is controlled by the encoder mechanism EC. The table 28 is fixed in the required position by means of the stoppers 44a and 44b. Then the surface analysis of the sample in the point of interest is carried out several times in accordance with a conventional practice by using several, e.g., three to five, multi-wavelength Raman spectroscopy probes 31 of the set, each having different angles of tilt of the light delivery beam to the surface of the sample and, hence, to the longitudinal axis of the Raman spectrometer. The test results that provide the most optimal signal/noise ratio are selected.

Upon completion of the first Raman spectroscopy test the table is released from the stoppers 44a and 44b and is turned to a position where the point of interest on the sample 30 is aligned with the wear test probe 26a' of the wear test unit 26a. Stopping of the rotary table 28 in a precise position under the wear test probe 26a' is controlled by the encoder EC mechanism. The table is fixed in the required position by means of the stoppers 44a and 44b. Wear test is then carried out in accordance with a conventional practice. Upon removal of the sample material to a predetermined depth from the surface of the sample in the point of interest, the table with the sample 30 is returned exactly to the same position as in the previous Raman spectroscopy test, and the surface analysis in the point of interest is repeated several times with the set of the multi-wavelength Raman spectroscopy probes 31. The test results that provide most optimal signal/noise ratio are selected. The steps of the tests with movement of the sample between the wear test unit and the Raman spectrometer are repeated as many time as needed by using different replaceable Raman spectroscopy probes of the set.

Thus, it has been shown that the apparatus of the invention is suitable for in-line testing and surface analysis of test materials where the test can be conducted with multiple sequential measurements of the material physical properties such as harness, resistance to wear, friction properties, etc., along with determination of material composition components and their distribution in the depth direction from the specimen surface revealed by using Raman spectroscopy. A specific rotary arrangements of measurement units with circular positioning of the measurement units above the sample provides high positioning accuracy unachievable with the linear arrangement of the units and thus allows precision repositioning of the multi-wavelength Raman spectroscopy probe head 31 in the same point for multiple measurements, which is especially important for Raman spectroscopy tests.

Although the invention has been shown and described with reference to specific embodiments, it is understood that these embodiments should not be construed as limiting the areas of application of the invention and that any changes and modifications are possible provided that these changes and modifications do not depart from the scope of the attached patent claims.

The invention claimed is:

1. A method for in-line testing and surface analysis of test material with participation of Raman spectroscopy comprising the steps of:
   (a) providing a material test apparatus having a stationary base plate that supports a vertical column, at least a wear test unit and a Raman spectrometer supported by the vertical column, a rotary table rotationally installed on the stationary base plate, and a sample holder that holds a sample to be tested in a position under the test units when the table rotates, the sample having a point of interest, the Raman spectrometer having a longitudinal axis, a laser unit with a plurality of lasers of different wavelength and being provided with a set of multi-wavelength Raman spectroscopy probes, wherein each multi-wavelength Raman spectroscopy probe has a laser, a plurality of light transmitting channels having optical fiber waveguides for delivery of laser light delivery beams from the laser unit to the point of interest on the sample, and a Raman radiation receiving channel arranged in the direction of said longitudinal axis, each channel having an optical fiber for propagation of a laser light of a specific wavelength;

(b) providing each multi-wavelength Raman spectroscopy probe of the set with a specific angle of tilt of the laser light delivery beams to the longitudinal axis;

(c) turning the rotary table into a position wherein the point of interest on the sample is aligned with the position of the multi-wavelength Raman spectroscopy probe;

(d) conducting surface analysis in the point of interest by using one multi-wavelength Raman spectroscopy probe of the set and by sequentially using the light transmitting channels of different wavelength;

(e) selecting the results of the surface analysis which provide the best signal/noise ratio;

(f) selecting another multi-wavelength Raman spectroscopy probe and conducting the steps (d) and (e) several times with other multi-wavelength Raman spectroscopy probes;

(g) turning the rotary table into a position wherein the point of interest on the sample is aligned with the position of the wear test unit;

(h) conducting the wear test until the material of the sample is removed to a predetermined depth;

(i) turning the rotary table into a position wherein the point of interest on the sample is aligned with the position of the multi-wavelength Raman spectroscopy probe installed in the Raman spectrometer;

(j) repeating the steps (f); and repeating the steps (i) and (j) for the remaining multi-wavelength Raman spectroscopy probes.

2. The method of claim 1, further comprising the steps of:

(k) providing each optical fiber waveguide with a micro-collimator installed on the way of the laser light delivery beam from the laser unit to the sample and with a common light-beam tilting lens which defines said specific angle of tilt of the laser light delivery beams to the longitudinal axis.

3. The method of claim 2, wherein the angle of tilt is selected in the range of 30° to 75°.

4. The method of claim 2, wherein the angle of tilt is selected in the range of 40° to 60°.

* * * * *